United States Patent
Zhu et al.

(10) Patent No.: US 10,203,317 B2
(45) Date of Patent: Feb. 12, 2019

(54) MULTI-FUNCTIONAL PRECIOUS STONE TESTING APPARATUS AND METHOD THEREOF

(71) Applicant: Shenzhen DiKai Industrial Co., Ltd., Shenzhen, Guangdong (CN)

(72) Inventors: Xiuling Zhu, Shenzhen (CN); Gary Bruce Peckham, Shenzhen (CN)

(73) Assignee: SHENZHEN DIKAI INDUSTRIAL CO., LTD., Shenzhen, Guangdong (CN)

( * ) Notice: Subject to any disclaimer, the term of this patent is extended or adjusted under 35 U.S.C. 154(b) by 175 days.

(21) Appl. No.: 15/241,024

(22) Filed: Aug. 18, 2016

(65) Prior Publication Data

US 2016/0363576 A1 Dec. 15, 2016

Related U.S. Application Data

(63) Continuation of application No. 14/564,041, filed on Dec. 8, 2014, now Pat. No. 9,453,808, which is a (Continued)

(51) Int. Cl.
*G01N 25/18* (2006.01)
*G01N 21/87* (2006.01)
(Continued)

(52) U.S. Cl.
CPC ........... *G01N 33/381* (2013.01); *G01N 21/63* (2013.01); *G01N 21/87* (2013.01);
(Continued)

(58) Field of Classification Search
CPC ........ G01N 25/18; G01N 30/66; G01N 25/20; G01N 27/041; G01N 33/381; G01N 2011/0093; G01N 21/87; G01N 21/63
(Continued)

(56) References Cited

U.S. PATENT DOCUMENTS 4,344,315 A * 8/1982 Moxon ................ G01N 33/381
374/44
4,344,677 A * 8/1982 Stuermer ........... G06K 15/1271
347/255

(Continued)

FOREIGN PATENT DOCUMENTS

GB 371421 A * 4/1932 ............... A24C 1/32

*Primary Examiner* — Gail Kaplan Verbitsky
(74) *Attorney, Agent, or Firm* — Raymond Y. Chan; David and Raymond Patent Firm

(57) ABSTRACT

A multi-functional precious stone testing apparatus includes a portable housing, a testing unit, and an indication unit. The portable housing includes a hand-held casing and a probe casing extended from a front end of the hand-held casing. The testing unit includes a conductive probe having a testing end portion extended out of a tip end of the probe casing for contacting a testing object to determine a conductivity of the testing object. The indication unit includes a LED light unit received in the hand-held casing for illuminating the testing end portion of the conductive probe during testing, wherein the LED light unit is positioned away from the tip end of the probe casing for preventing heat generated from the LED light unit being transmitted toward the conductive probe to affect an accurate measurement for the conductivity of the testing object.

7 Claims, 7 Drawing Sheets

Related U.S. Application Data continuation-in-part of application No. 12/932,109, filed on Feb. 16, 2011, now Pat. No. 8,947,111.

(51) Int. Cl.
| | | |
|---|---|---|
| *G01N 21/63* | (2006.01) | |
| *G01N 33/38* | (2006.01) | |
| *G01N 27/04* | (2006.01) | |
| *G01N 21/88* | (2006.01) | |

(52) U.S. Cl.
CPC ......... *G01N 21/8803* (2013.01); *G01N 25/18* (2013.01); *G01N 27/041* (2013.01)

(58) Field of Classification Search
USPC .................. 374/44, 163; 324/715, 696, 702; 340/540
See application file for complete search history.

(56) References Cited

U.S. PATENT DOCUMENTS

| | | | | |
|---|---|---|---|---|
| 4,445,367 A | * | 5/1984 | Goldsmid | G01N 3/42 374/45 |
| 5,118,181 A | * | 6/1992 | Yifrach | G01N 21/87 250/461.1 |
| 5,559,436 A | * | 9/1996 | Matthews | G01N 27/72 324/228 |
| 5,835,205 A | * | 11/1998 | Hunter | G01N 21/87 356/30 |
| 5,955,735 A | * | 9/1999 | Coleman | G01N 33/381 250/336.1 |
| 6,043,742 A | * | 3/2000 | Austin | G01N 21/87 250/461.1 |
| 6,265,884 B1 | * | 7/2001 | Menashi | G01N 27/041 324/693 |
| 6,281,680 B1 | * | 8/2001 | Matthews | G01N 27/72 324/228 |
| 6,439,766 B1 | * | 8/2002 | Nelson | G01N 33/381 324/693 |
| 7,126,351 B2 | * | 10/2006 | Claus | G01N 27/041 324/663 |
| 8,947,111 B2 | * | 2/2015 | Zhu | G01N 25/18 324/717 |
| 9,176,068 B1 | * | 11/2015 | Radomyshelsky | G01J 1/58 |
| 9,439,595 B2 | * | 9/2016 | Leininger | A61B 5/0004 |
| 9,453,808 B2 | * | 9/2016 | Zhu | G01N 21/87 |
| 9,469,918 B2 | * | 10/2016 | Xu | C30B 25/02 |
| 2014/0292358 A1 | * | 10/2014 | Kessler | G01N 25/18 324/693 |
| 2014/0337035 A1 | * | 11/2014 | Kessler | G01N 33/381 704/274 |
| 2016/0178168 A1 | * | 6/2016 | Didur | F21V 19/003 206/6.1 |
| 2018/0172599 A1 | * | 6/2018 | Wang | G01N 21/645 |

* cited by examiner

MULTI-FUNCTIONAL PRECIOUS STONE TESTING APPARATUS AND METHOD THEREOF

CROSS REFERENCE OF RELATED APPLICATION

This is a Continuation application that claims of priority under 35 U.S.C. § 119 to a U.S. non-provisional application Ser. No. 14/564,041, filed Dec. 8, 2014, which is Continuation-In-Part application that claims the benefit of priority under 35 U.S.C. § 119 to a non-provisional application Ser. No. 12/932,109, filed Feb. 16, 2011, now U.S. Pat. No. 8,947,111.

BACKGROUND OF THE PRESENT INVENTION

Field of Invention

The present invention relates to a precious stone tester, and more particular to a multi-functional precious stone testing apparatus and method thereof, which comprises a LED light unit for providing an illumination at the conductive probe for determining thermal and/or electrical conductivity when the conductive probe contacts with the testing object without substantially transmitting heat from the LED light unit to the conductive probe.

Description of Related Arts

A gemstone tester is considered as one of the convenient tools for gemstone (such as diamond, moissanite and other precious stones) identification. A conventional gemstone tester comprises a testing probe for determining a thermal conductivity of the gemstone such as diamond as well as an electrical conductivity of moissanite in order to classify the gemstone by its physical properties. However, the gemstone tester has several drawbacks. The user must be proficient in the relevant skill and techniques to operate the gemstone tester and with a relatively practical understanding of the theoretical principles of gemstone because the gemstone tester must be adjusted or regulated its parameters during testing operation. The testing errors will be obtained due to the insufficient sensitivity of the gemstone tester or the improper operation of the gemstone tester. In addition, the gemstone tester can only test a particular gemstone. Therefore, it is a hassle for the user to carry different gemstone tester in order to test various kinds of gemstones. Furthermore, the gemstone tester can only identify whether the gemstone is real, however, the gemstone tester cannot measure the fluorescence of gemstones through the visible light. In other words, the user must carry another tester in order to measure the fluorescence of gemstones.

An improved gemstone tester further comprises an illumination unit for illuminating the testing probe when the testing probe contacts with the gemstone. The illumination unit comprises a light-up frame, wherein the light-up frame forms a tip holding frame to retain the testing probe in position. In other words, the testing probe is extended through and supported at the light-up frame. Therefore, the light-up frame provides enough illumination at the tip of the testing probe in order to accurately contact the tip of the testing probe at the gemstone.

However, the illumination unit not only generates light to the light-up frame but also generates heat toward the testing probe because the illumination unit is positioned close to the testing probe. Since the testing probe is arranged for determining the conductivity of the gemstone, heat from the illumination unit will affect the accuracy of conductivity of the gemstone.

SUMMARY OF THE PRESENT INVENTION

The invention is advantageous in that it provides a multi-functional precious stone testing apparatus and method thereof, which comprises a LED light unit for providing an illumination at the conductive probe when the conductive probe contacts with the testing object without substantially transmitting heat from the LED light unit to the conductive probe.

Another advantage of the invention is to provide a multi-functional precious stone testing apparatus and method thereof, which can accurately classify the testing object as one of Moissanite, diamond, metal, and other stone.

Another advantage of the invention is to provide a multi-functional precious stone testing apparatus and method thereof, which comprises a UV light source for generating a UV light beam toward the testing object to measure the fluorescence of the testing object. In particular, the conductive probe and the UV light source are operated independently.

Another advantage of the invention is to provide a multi-functional precious stone testing apparatus and method thereof, wherein the light transmissible frame is coupled between the hand-held casing and the probe casing to diffuse the light from the LEDs for illumination of the testing end portion of the conductive probe.

Another advantage of the invention is to provide a multi-functional precious stone testing apparatus and method thereof, wherein the operation of the present invention is simple and easy by contacting the thumb and index finger of the user at the touch control and by contacting the testing end portion of the conductive probe at the testing object.

Another advantage of the invention is to provide a multi-functional precious stone testing apparatus and method thereof, wherein the LED indentifying indicators are formed on the top wall of the portable housing for easy reading.

Additional advantages and features of the invention will become apparent from the description which follows, and may be realized by means of the instrumentalities and combinations particular point out in the appended claims.

According to the present invention, the foregoing and other objects and advantages are attained by a multi-functional precious stone testing apparatus, which comprises a portable housing, a testing unit, and an indication unit.

The portable housing comprises a hand-held casing for receiving a power source therein, and a probe casing extended from a front end of the hand-held casing.

The testing unit comprises an evaluation circuit received in the hand-held casing and electrically linked with the power source, and a conductive probe operatively linked to the evaluation circuit, wherein the conductive probe has a testing end portion extended out of a tip end of the probe casing for contacting a testing object to determine a thermal and electrical conductivity of the testing object.

The indication unit comprises a LED light unit received in the hand-held casing and operatively linked to the evaluation circuit for generating a light indicating effect to identify the testing object in responsive to the conductivity of the testing object and for illuminating the testing end portion of the conductive probe during testing, wherein the LED light unit is positioned away from the tip end of the probe casing for preventing heat generated from the LED light unit being transmitted toward the conductive probe to affect an accurate measurement for the thermal and/or electrical conductivity of the testing object.

In accordance with another aspect of the invention, the present invention comprises a method of classifying a testing object by a multi-functional precious stone testing apparatus which comprises a hand-held casing and a probe casing extended therefrom, wherein the method comprises the following steps.

(1) Determine a thermal and/or electrical conductivity of the testing object by contacting a testing end portion of a conductive probe of a conduction unit of the testing unit to the testing object, wherein the testing end portion of the conductive probe is extended out of a tip end of the probe casing.

(2) Illuminate the testing end portion of the conductive probe by a LED light unit which is positioned away from the tip end of the probe casing for preventing heat generated from the LED light unit being transmitted toward the conductive probe to affect an accurate measurement for the thermal and/or electrical conductivity of the testing object.

(3) Activate one of a plurality of indicating lights in responsive to the corresponding conductivity of the testing object to classify the testing object as one of Moissanite, diamond, metal, and other stone.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
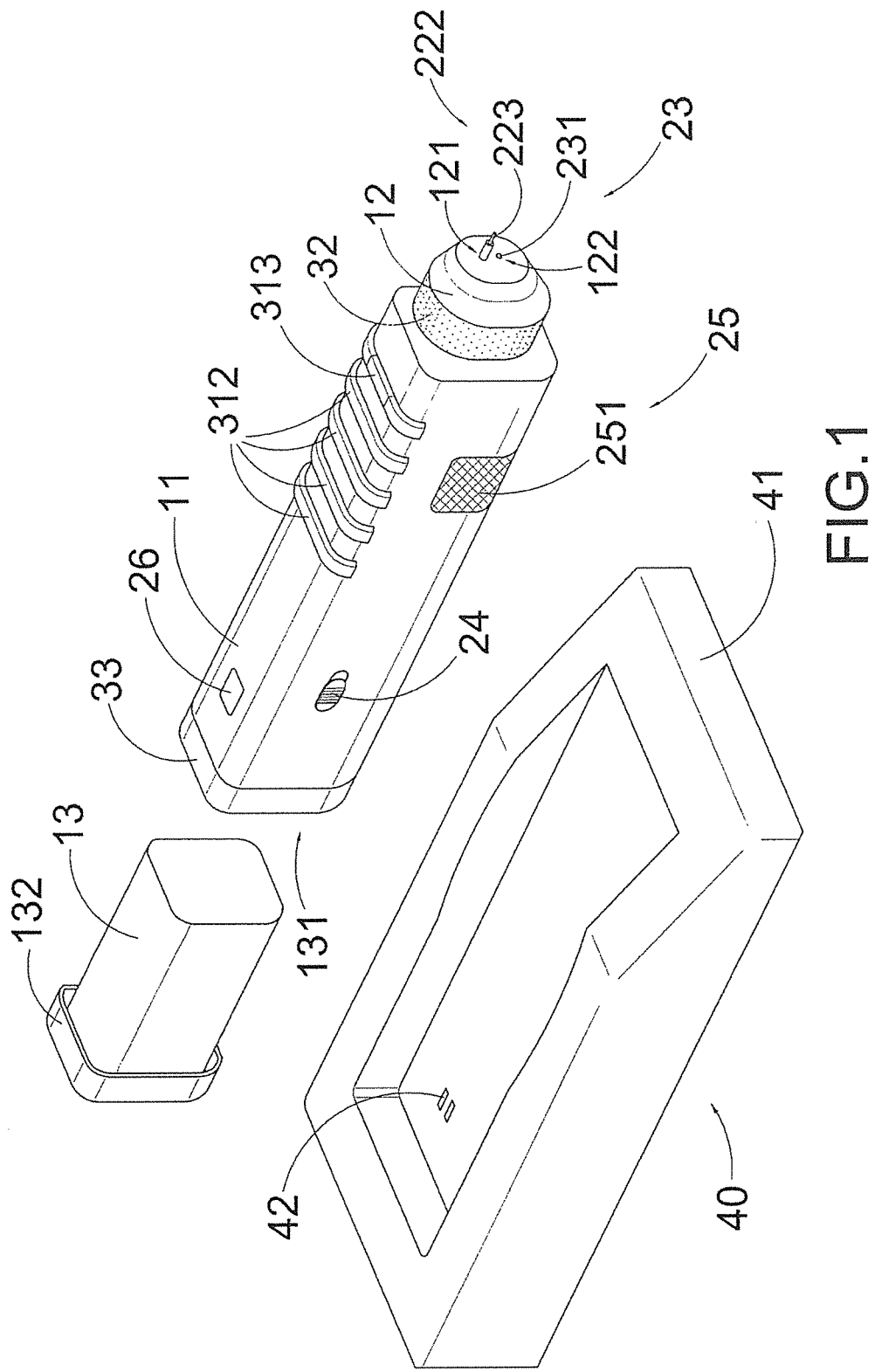
FIG. 1 is a perspective view of a multi-functional precious stone testing apparatus according to a preferred embodiment of the present invention.
Figure 2:
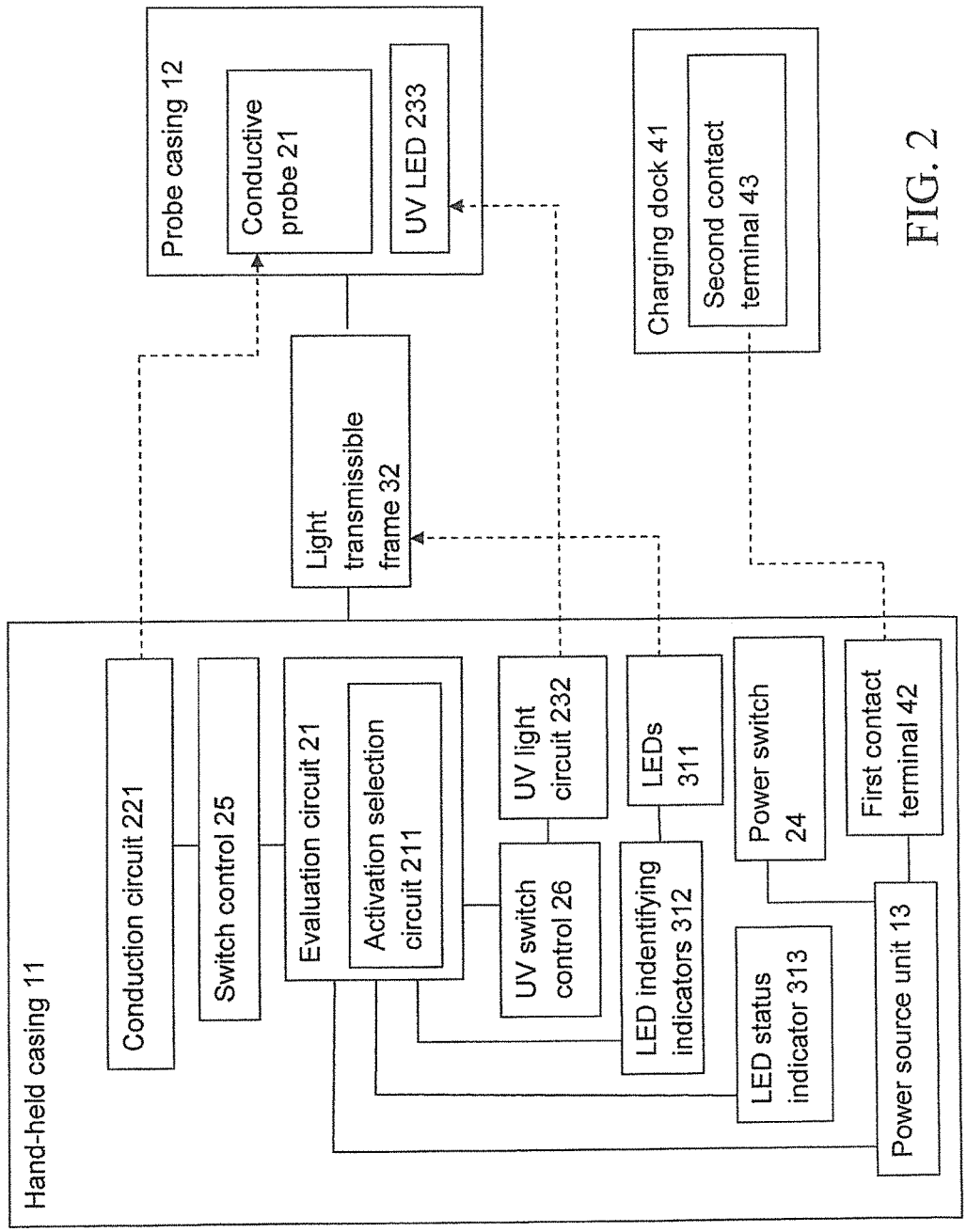
FIG. 2 is a block diagram of the multi-functional precious stone testing apparatus according to the above preferred embodiment of the present invention.

Referring to FIGS. 1 and 2 of the drawings, a multi-functional precious stone testing apparatus according to a preferred embodiment of the present invention is illustrates, wherein the multi-functional precious stone testing apparatus, which is adapted for identifying a testing object as one of diamond, Moissanite, metal, and other stone, comprises a portable housing 10, a testing unit 20, and an indication unit 30.

The portable housing 10 comprises a hand-held casing 11 for receiving a power source unit 13 therein, and a probe casing 12 extended from a front end of the hand-held casing 11. Accordingly, the hand-held casing 11 preferably has a top wall, a bottom wall, and two sidewalls to define an interior cavity within the top wall, bottom wall, and sidewalls, wherein the power source unit 13 is received in the interior cavity of the hand-held casing 11.

The testing unit 20 comprises an evaluation circuit 21 received in the interior cavity of the hand-held casing 11 and electrically linked with the power source unit 13, and a conduction unit 22 operatively linked to the evaluation circuit 21.

The evaluation circuit 21 is a microprocessor electrically coupled at a circuit board with a preloaded evaluation program, wherein the evaluation circuit 21 is arranged to receive a testing signal from the conduction unit 22.

Accordingly, the conduction unit 22 comprises a conduction circuit 221 electrically linked to the evaluation circuit 21 and a conductive probe 222 which is substantially supported by the probe casing 12 and operatively linked to the conduction circuit 221 for determining thermal and/or electrical conductivity when the conductive probe 222 contacts with a testing object.

The conductive probe 222 has a testing end portion 223 extended out of a tip end of the probe casing 12 for contacting the testing object to determine a thermal and/or electrical conductivity of the testing object. Generally, the conductive probe 222 determines a thermal conductivity of a gemstone such as diamond and an electrical conductivity of a moissanite. In other word, the testing signal is sent from the conductive probe 222 to the evaluation circuit 21 such that evaluation circuit 21 will analysis the testing signal in responsive to the conductivity of the testing object in order to classify the testing object.

The testing unit 20 further comprises a UV light source 23 received in the portable housing 10 for generating a UV light beam toward the testing object to measure the fluorescence of the testing object, wherein the UV light source 23 has a light head 231 extended out of the tip end of the probe casing 12 at a position adjacent to the testing end portion 223 of the conductive probe 222.

According to the preferred embodiment, the UV light source 23 comprises a UV light circuit 232 received in the hand held casing 11 to electrically linked with the evaluation circuit 21 and a UV LED 233 adapted for UV light generation, wherein the light head 231 is defined at a head portion of the UV LED 233 protruding out of the tip end of the probe casing 12.

As shown in FIG. 1, the probe casing 12, having a conical shape, has a tip end surface defining a first through slot 121 and a second through slot 122 spacedly formed at the tip end surface, wherein the testing end portion 223 of the conductive probe 222 is extended out of the tip end of the probe casing 12 through the first through slot 121 while the light head 231 of the UV light source 23 is extended out of the tip end of the probe casing 12 through the second through slot 122. Therefore, the testing end portion 223 of the conductive probe 222 is positioned adjacent to the light head 231 of the UV light source 23.

In addition, the protruding length of the testing end portion 223 of the conductive probe 222 is substantially longer than the protruding length of light head 231 of the UV light source 23, such that the testing end portion 223 of conductive probe 222 not only forms a contact point for measuring the thermal and/or electrical conductivity of the testing object but also forms a support point for retaining the light head 231 of the UV light source 23 at a position spacedly apart from the testing object when the testing end portion 223 of the conductive probe 222 contacts with the testing object.

The evaluation circuit 21 comprises an activation selection circuit 211 operatively linked to the conduction unit 22 and the UV light source 23 to selectively operate the conductive probe 222 and the UV light source 23 independently.

Accordingly, the testing unit 20 further comprises a power switch 24 provided at the hand-held casing 11 to electrically link between the power source unit 13 and the evaluation circuit 21 in order to selectively control the evaluation circuit 21 in an on-and-off manner.

The testing unit 20 further comprises a switch control 25 operatively linked to the activation selection circuit 211 to selectively control the conduction unit 22, wherein when the switch control 25 is actuated, the conduction unit 22 is activated through the activation selection circuit 211 to determine the thermal and/or electrical conductivity of the testing object when the conductive probe 222 contacts with the testing object.

Accordingly, the switch control 25 comprises two touch controls 251 provided at the sidewalls of the hand-held casing 11 respectively, wherein the touch controls 251 are activated by a touch of the user. In other words, when the user (right-handed user) holds the hand-held casing 11, the thumb and the index finger of the user will contact at the touch controls 251 respectively in order to activate the conduction unit 22 is activated through the activation selection circuit 211. When one of the touch controls 251 is untouched, the activation selection circuit 211 will automatically deactivate the conduction unit 22 to stop the operation of the conduction unit 22.

The testing unit 20 further comprises a UV switch control 26 operatively linked to the activation selection circuit 211 to selectively control the UV light source 23, wherein when the UV switch control 26 is actuated, the UV light source 23 is activated through the activation selection circuit 211 for UV light generation to measure the fluorescence of the testing object. The UV switch control 26 is preferably provided at the top wall of the hand-held casing 11 such that when the user actuate the UV switch control 26, preferably by depression of the UV switch control 26, the UV light source 23 is activated for UV light generation. It is worth mentioning that the conduction unit 22 and the UV light source 23 are operated independently. In addition, the conduction unit 22 and the UV light source 23 can be operated at the same time.

According to the preferred embodiment, the indication unit 30 comprises a LED light unit 31 received in the hand-held casing 11 and operatively linked to the evaluation circuit 21 for generating a light indicating effect to identify the testing object in responsive to the conductivity of the testing object and for illuminating the testing end portion of the conductive probe 222 during testing.

According to the preferred embodiment, the LED light unit 31 is positioned away from the tip end of the probe casing 12 for preventing heat generated from the LED light unit 31 being transmitted toward the conductive probe 222 to affect an accurate measurement for the conductivity of the testing object.

The LED light unit 31 comprises a plurality of LEDs 311 coaxially supported within the hand-held casing 11 at a position close to the front end thereof, wherein the LEDs 311 are activated for generating light effect when the evaluation circuit 21 is activated. In addition, the evaluation circuit 21 is activated when the conductive probe 222 is in good-contact with the testing object. Therefore, the LEDs 311 will be activated as an indicator for ensuring the testing end portion 223 of the conductive probe 222 being in good-contact with the testing object and as an illuminator for illuminating at the testing end portion 223 of the conductive probe 222 to be contacted with the testing object. However, since the LEDs 311 are positioned away from the testing end portion 223 of the conductive probe 222, the heat from the LEDs 311 will not be transmitted to the conductive probe 222 in order to determine the conductivity of the testing object. It is worth mentioning that the LED light unit 31 is also positioned away from the light head 231 of the UV light source 23 for preventing any interference of the UV light with respect to the illumination light.

Preferably, the LEDs 311 will be activated only when the conduction unit 22 is activated. In other words, the LEDs 311 will be automatically switched off during the operation of the UV light source 23.

The indication unit 30 further comprises a light transmissible frame 32 coupled between the hand-held casing 11 and the probe casing 12, wherein the LEDs 311 of the LED light unit 31 are aligned with the light transmissible frame 32 such that when the evaluation circuit 21 is activated, the LEDs 311 of the LED light unit 31 generate an illumination light to light up the light transmissible frame 32 to diffuse the light from the LEDs 311 for illumination of the testing end portion 223 of the conductive probe 222. In other words, when the conductive probe 222 is in good-contact with the testing object to activate the evaluation circuit 21, the light transmissible frame 32 is lightened up by the LEDs 311 in responsive to the contact between the conductive probe 222 and the testing object.

Figure 3:
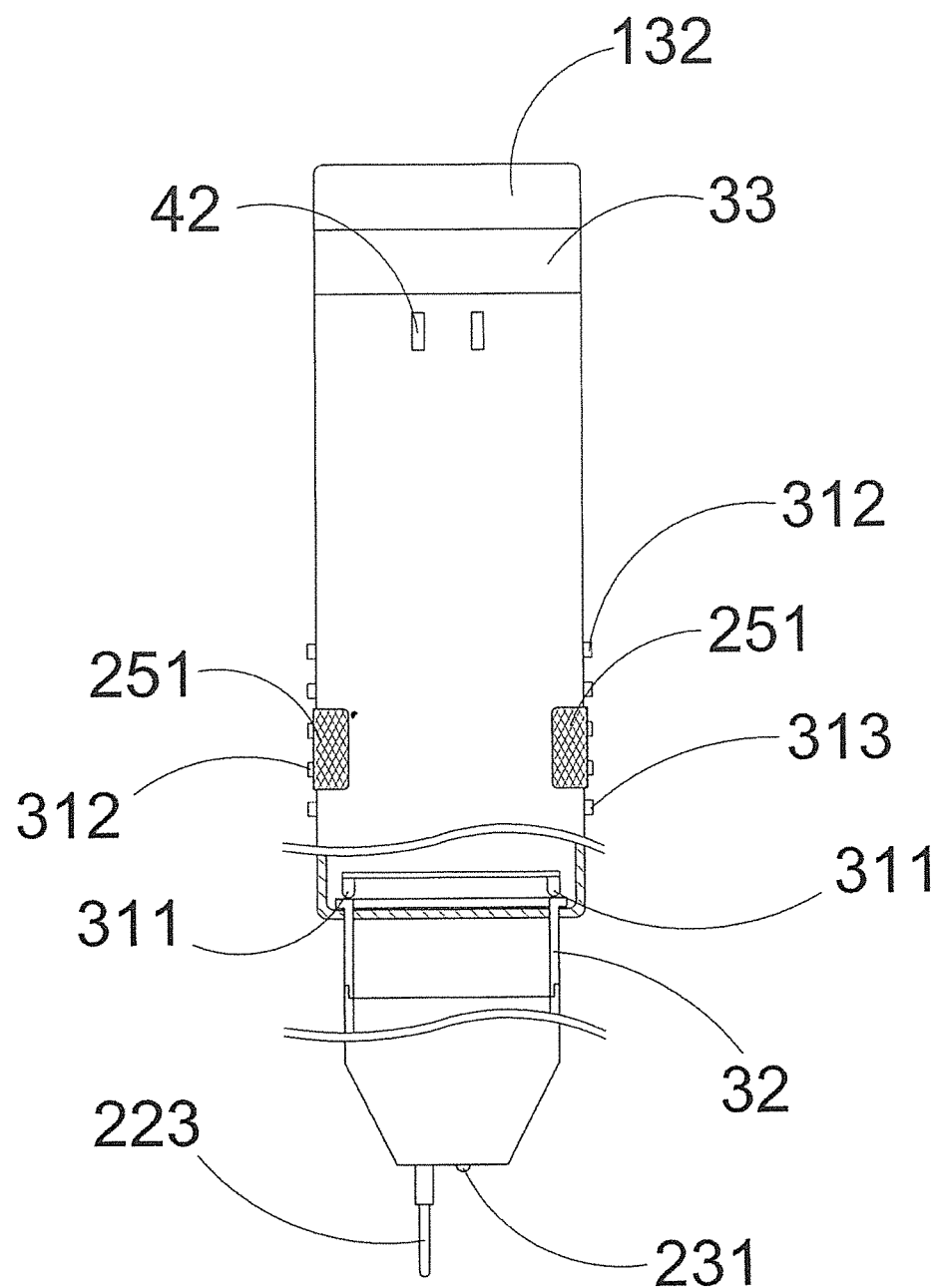
FIG. 3 is a partially sectional view of the multi-functional precious stone testing apparatus according to the above preferred embodiment of the present invention, illustrating the LEDs and the light transmissible frame at the hand-held casing for illumination.

As shown in FIGS. 1 and 3, the light transmissible frame 32 is formed in ring shape encircling around the probe casing 12, wherein the light transmissible frame 32 is detachably coupled between the hand-held casing 11 and the probe casing 12. When the LEDs 311 are activated for light generation, the light transmissible frame 32 forms a 360° illuminated ring to illuminate the testing end portion 223 of the conductive probe 222. Preferably, the light transmissible frame 32 is made of transparent material such as clear plastic or glass, or translucent material such as frosted plastic or acrylic.

The light transmissible frame 32 has a rear rim extended from the front end of the hand-held casing 11 and a front rim extended to the probe casing 12. In other words, the light transmissible frame 32 forms a neck portion of the portable housing 10 between the hand-held casing 11 and the probe casing 12. Accordingly, the LEDs 311 are coaxially supported at the hand-held casing 11 to align with the rear rim of the light transmissible frame 32, such that when the LEDs 311 are activated for light generation, the light will be transmitted from the rear rim of the light transmissible frame 32 to the front rim thereof so as to light up the light transmissible frame 32.

In addition, the light transmissible frame 32 also forms as a heat isolation frame between the hand-held casing 11 and the probe casing 12 for preventing the heat from the LEDs 311 being transmitted to the conductive probe 222.

The LED light unit 31 further comprises a plurality of LED indentifying indicators 312 spacedly provided on the top wall of the hand-held casing 11 for indicating the testing object to be classified as one of diamond, Moissanite, metal, and other stone. Accordingly, the LED indentifying indicators 312 are operatively linked to the evaluation circuit 21 to show the result of the testing evaluation. The LED indentifying indicators 312 comprises a "diamond" indentifying indicator, "Moissanite" indentifying indicator, "metal" indentifying indicator, and "other stone" indentifying indicator, wherein the respective LED indentifying indicator 312 is activated in responsive to the conductivity of the testing object through the evaluation circuit 21.

Preferably, the LED indentifying indicators 312 are arranged for generating different colors for easy identification. For example, the "diamond" indentifying indicator will generate first color for identifying the testing object as diamond. The "Moissanite" indentifying indicator will generate second color for identifying the testing object as Moissanite. The "metal" indentifying indicator will generate third color for identifying the testing object as metal. The "other stone" indentifying indicator will generate fourth color for identifying the testing object as other stone. In addition, the LEDs 311 will simultaneously change the color to match with the color of the corresponding indentifying indicator 312 when the test is completed. According to the preferred embodiment, different colors are used to represent different test result, such as Blue color representing Diamond, Green color representing Moissanite, Amber (Orange) color representing Metal, and Red color representing Stone.

The LED light unit 31 further comprises a LED status indicator 313 provided at the top wall of the hand-held casing 11 for indicating the status of the evaluation circuit 21. Accordingly, the LED status indicator 313 is arranged for generating different colors in order to indicate the status of the evaluation circuit 21. For example, the LED status indicator 313 will generate red color when the power switch 24 is actuated to start activating the evaluation circuit 21. The LED status indicator 313 will generate amber color to indicate the evaluation circuit 21 being ready for operation. The LED status indicator 313 will generate green color when both fingers are positioned well making a good conductive circuit ready for testing. In operation, firstly, the user turns on the tester, the red wait light illuminates whilst the tester warms up all four testing circuits. Then, the amber light illuminates informing the user to position his or her fingers (such as thumb and index fingers) on to the testing plate positions. Finally, if the user has positioned his or her fingers well and correctly, the green light will illuminates informing the user that he or she is now ready to perform the test. If at any point the amber light comes back on and the green light goes off, it informs the user that he or she does not have a good contact between his or her fingers and the testing plates.

According to the preferred embodiment, the power source unit 13 comprises a battery compartment 131 in the hand-held casing 11 for receiving a battery therein to electrically link with the evaluation circuit 21, and a compartment cover 132 detachably coupled at a rear end of the hand-held casing 11 to enclose the battery compartment 131. The battery can be a replaceable battery replace ably received in the battery compartment 131. Preferably the battery is a rechargeable battery received in the battery compartment 131.

As shown in FIG. 1, the indication unit 30 may further comprise a light indication frame 33 coupled between the rear end of the hand-held casing 11 and the compartment cover 132, wherein the LEDs 311 of the LED light unit 31 generate an illumination light to light up the light indication frame 33 corresponding to the light transmissible frame 32. Therefore, the light transmissible frame 32 and the light indication frame 33 are formed at the front and rear ends of the hand-held casing 11. It is worth mentioning that due to the preference of the buyers, it is an option to have just the light transmissible frame 32 or to have both the light transmissible frame 32 as well as the light indication frame 33 as illustrated in the FIG. 1 according to the preferred embodiment.

Accordingly, the multi-functional precious stone testing apparatus further comprises a charging arrangement 40 for electrically charging the power source unit 13, wherein the charging arrangement 40 comprises a charging dock 41 for electrically linking to a power supply, a first contact terminal 42 provided at the portable housing 10 to electrically link with the power source unit 13, and a second contact terminal 43 provided at the charging dock 41 and arranged in such a manner that when the portable housing 10 docks at the charging dock 41, the first contact terminal 42 contacts with the second contact terminal 43 to electrically charge the power source unit 13.

In order operate the multi-functional precious stone testing apparatus, the user is able to switch on the power switch 24 in order to warm up the evaluation circuit 21, wherein the LED status indicator 313 will generate red color during the warm up time. Once the LED status indicator 313 generates amber color, the evaluation circuit 21 is ready for operation. The user is able to hold the hand-held casing 11 and to contact the touch controls 251 by the thumb and the index finger respectively to activate the conduction unit 22. Once the testing end portion 223 of the conductive probe 222 contacts with the testing object, the LED status indicator 313 will generate green color to indicate the proper contacts of the touch controls 251 and the good contact between the testing end portion 223 of the conductive probe 222 and the testing object. Then, the evaluation circuit 21 will classify the testing object in responsive to the conductivity thereof. Correspondingly, one of the LED indentifying indicators 312 will be activated for light indication by the evaluation circuit 21.

The user is also able to measure the fluorescence of the testing object via the UV light source 23. The user is able to actuate the UV switch control 26 in order to activate the UV light source 23 for UV light generation. It is worth mentioning that the light head 231 of the UV light source 23 is spaced apart from the testing object since the testing end portion 223 of the conductive probe 222 contacts with the testing object.

Figure 4:
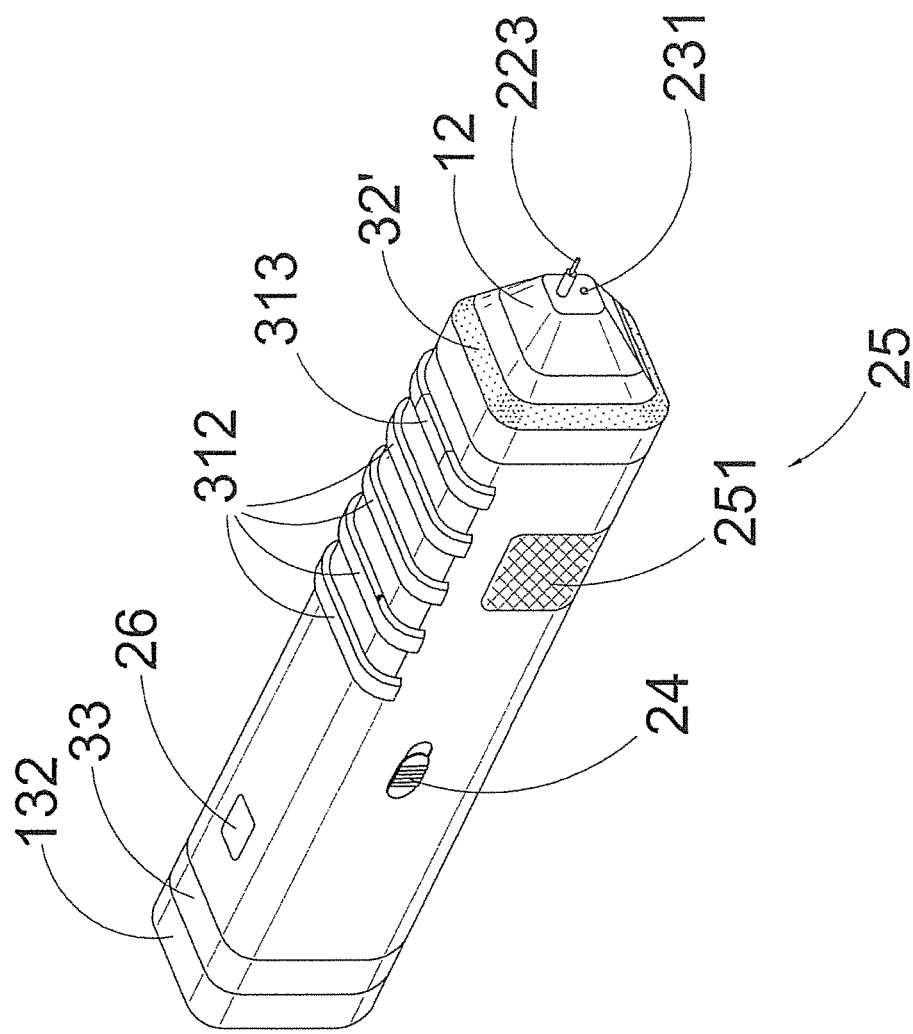
FIG. 4 illustrates an alternative mode of the light transmissible frame of the multi-functional precious stone testing apparatus according to the above preferred embodiment of the present invention.

FIG. 4 illustrates an alternative mode of the light transmissible frame 32' wherein the light transmissible frame 32' is formed in ring shape integrally formed at the front end of the hand-held casing 11 to encircle around the probe casing 12. The LEDs 311 of the LED light unit 31 are aligned with the light transmissible frame 32' such that when the evaluation circuit 21 is activated, the LEDs 311 of the LED light unit 31 generate an illumination light to light up the light transmissible frame 32' to diffuse the light from the LEDs 311 for illumination of the testing end portion 223 of the conductive probe 222.

Figure 5:
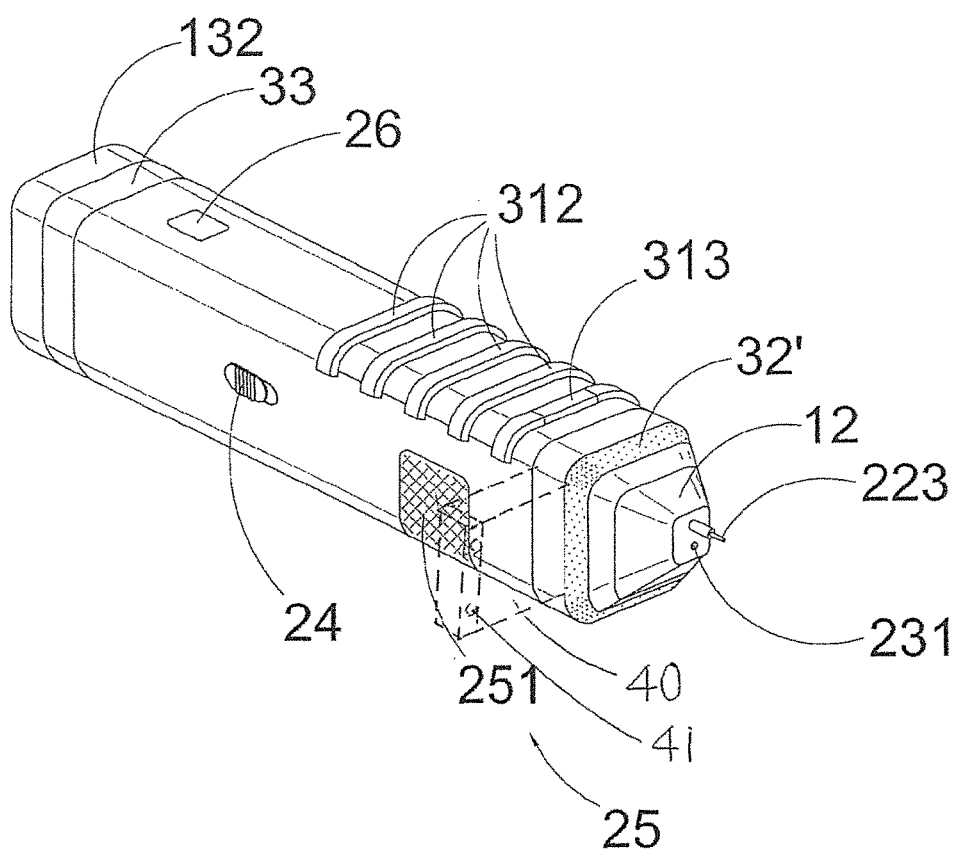
FIG. 5 illustrates a first alternative mode of the multi-functional precious stone testing apparatus according to the above preferred embodiment of the present invention.

FIG. 5 illustrates another alternative mode of the preferred embodiment of the present invention, wherein a magnifying lens 40 can be mounted to the testing apparatus of the present invention, in foldable or slidable manner, at a predetermined position adapted for the user to view the conductive probe 222 to magnify the conductive probe 222 and the object being tested. The magnifying lens 40 may further comprise at least a LED 41 for illuminating the area around the magnifying lens 40 during magnifying the testing operation.

Figure 6:
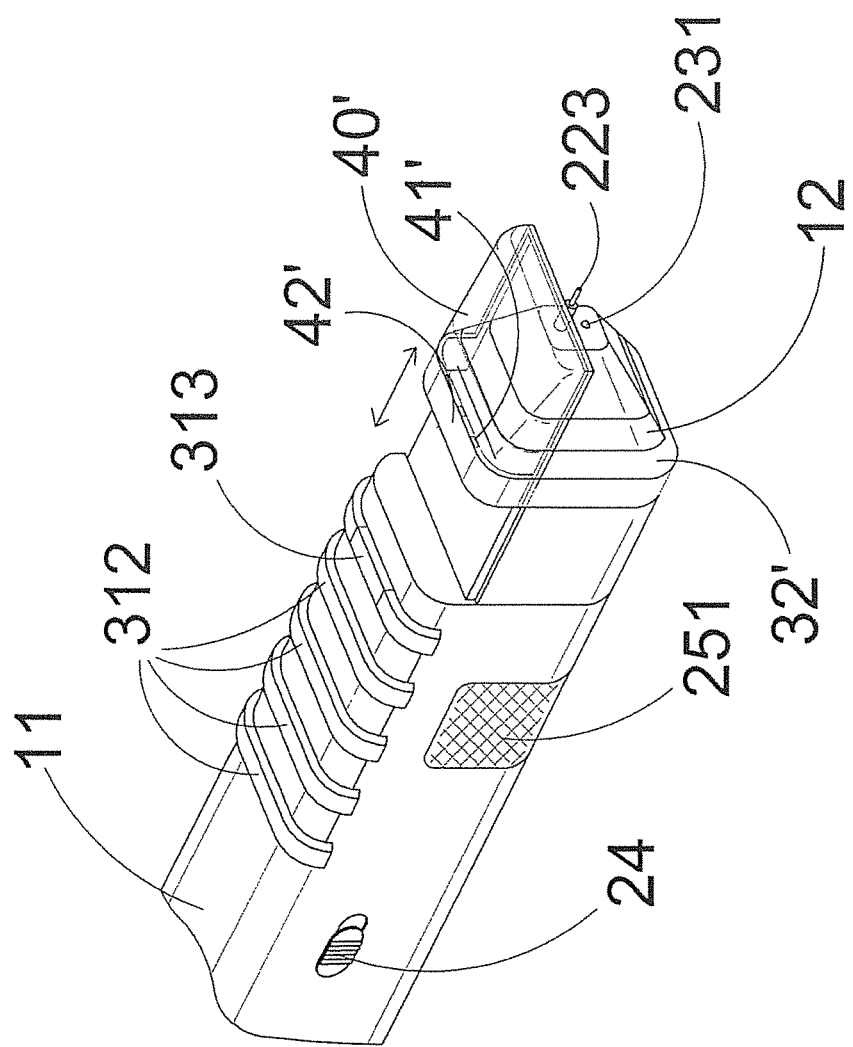
FIG. 6 illustrates a second alternative mode of the multi-functional precious stone testing apparatus according to the above preferred embodiment of the present invention.

FIG. 6 illustrates another alternative mode of the preferred embodiment of the present invention, wherein the magnifying lens 40' is movably coupled at the hand-held casing 11 at a position close to the front end thereof. The magnifying lens 40' is adapted to slidably move between a folded position and an unfolded position, wherein at the folded position, the magnifying lens 40' is rearwardly slid on the outer surrounding surface of the hand-held casing 11, preferably at the top wall thereof, and at the unfolded position, the magnifying lens 40' is frontwardly slid toward the conductive probe 22 to magnify the conductive probe 222 and the object being tested. A lens frame 42' with one or more LED light illuminators 41' can be slidably mounted at the top wall of the hand-held casing 11 to hold the magnifying lens 40' in position. The LED light illuminator 41' of the lens frame 42' is electrically linked to the power source unit 13 via a positioning contact switch that when the magnifying lens 40' is moved at the folded position, the LED light illuminator 41' of the lens frame 42' is electrically disconnected to the power source unit 13 and when the magnifying lens 40' is moved at the unfolded position, the LED light illuminator 41' of the lens frame 42' is electrically connected to the power source unit 13.

Figure 7:
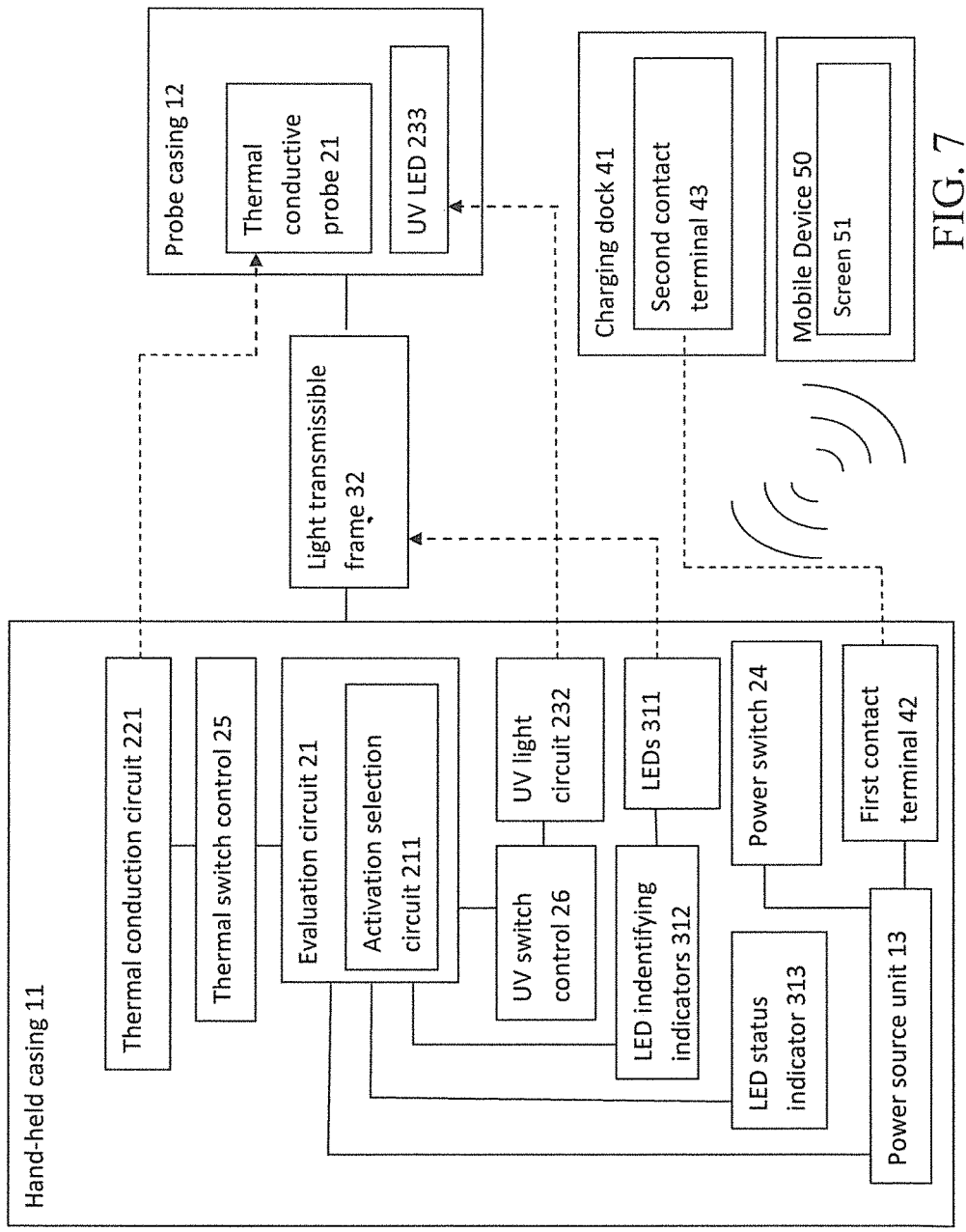
FIG. 7 is a block diagram of the multi-functional precious stone testing apparatus equipped and configured with a mobile device through a wireless network according to the above preferred embodiment of the present invention.

It is worth mentioning that, referring to FIG. 7, the multi-functional precious stone testing apparatus according the preferred embodiment as shown in FIGS. 1-6 of the present invention may further include a communication module linked with, but not limited to, the evaluation circuit 21, UV light circuit 232, UV switch control 26, LED indentifying indicator 312, LED status indicator 313, power source unit 13, thermal conductive probe 21, thermal switch control 25, and/or thermal conduction circuit 221, to be equipped and configured with a mobile device 50, such as mobile phone, tablet, notebook, and etc., of the user which has been downloaded with a corresponding APP through a wireless network, such as Internet, Wi-Fi, Bluetooth, and etc., so as to illustrate the test results, indicating the testing object to be classified as one of diamond, Moissanite, metal and other stone, as well as acting as the indication unit 30, if required, so that the user may simply access the test result from his or her paired mobile device placed at where it is convenient for the user to view. Accordingly, it would be an alternative mode of the multi-functional precious stone testing apparatus of the present invention that by equipping and configuring with the APP of the mobile device of the user, the mobile device can substitute the indication unit 30 of the present invention. In other words, the mobile device 50 paired with the multi-functional precious stone testing apparatus can be functioned as the indication device 30 which is wirelessly linked and configured with the evaluation circuit 21 through the wireless network for generating an indicating effect to identify the testing object in responsive to the conductivity of the testing object and for illuminating the testing end portion of the conductive probe 222 during testing, wherein the indication unit 30 is configured that when the conductive probe 222 is in contact with the testing object to activate the evaluation circuit 21, the indication unit 30 generates a testing signal in responsive to the contact between the conductive probe and the testing object to identify the testing object as diamond by the thermal conductivity and as moissanite by the electrical conductivity.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of classifying a testing object by a multi-functional precious stone testing apparatus which comprises a hand-held casing and a probe casing extended therefrom, comprising the steps of:
   (a) determining a conductivity of the testing object by contacting a testing end portion of a conductive probe of a conduction unit of said testing unit to the testing object, wherein said testing end portion of said conductive probe is extended out of a tip end of said probe casing;
   (b) illuminating said testing end portion of said conductive probe by an illumination light, wherein said illumination light is supported within said hand-held casing and is positioned away from said tip end of said probe casing for preventing heat generated from said illumination light being transmitted toward said conductive probe to affect an accurate measurement for said conductivity of the testing object; and
   (c) activating one of a plurality of indicating lights in responsive to said corresponding conductivity of the testing object to classify the testing object as one of Moissanite, diamond, metal, and other stone.

2. The method, as recited in claim 1, wherein the step (a) further comprises the steps of:
   (a.1) contacting the testing object with said conductive probe and activating two touch controls of a switch control when an index finger and a thumb of an user who is holding said hand-held casing are contacting at two said touch controls respectively;
   (a.2) activating said conduction unit through an activation selection circuit;
   (a.3) determining a thermal conductivity or electrical conductivity of said testing object while said conductive probe contacting with the testing object; and
   (a.4) sending a testing signal to an evaluation circuit to analysis said testing signal in responsive to said conductivity of the testing object to identify the testing object as diamond by said thermal conductivity and a moissanite by said electrical conductivity.

3. The method, as recited in claim 1, wherein the step (b) further comprises a step of prevent heat generated from said illumination light from being transmitted toward said conductive probe by providing a distance between said illumination light and said tip end of said probe casing so as to ensure an accurate measurement for said thermal conductivity or said electrical conductivity of the testing object, wherein said illumination light is a LED light.

4. The method, as recited in claim 2, wherein the step (b) further comprises a step of prevent heat generated from said illumination light from being transmitted toward said conductive probe by providing a distance between said illumination light and said tip end of said probe casing so as to ensure an accurate measurement for said thermal conductivity or said electrical conductivity of the testing object, wherein said illumination light is a LED light.

5. The method, as recited in claim 1, further comprising a step of deactivating said conduction unit through said activation selection circuit when one of said touch controls is untouched by the user.

6. The method, as recited in claim 2, further comprising a step of deactivating said conduction unit through said activation selection circuit when one of said touch controls is untouched by the user.

7. The method, as recited in claim 3, further comprising a step of deactivating said conduction unit through said activation selection circuit when one of said touch controls is untouched by the user.

* * * * *